United States Patent
Olken et al.

(10) Patent No.: US 8,263,404 B2
(45) Date of Patent: Sep. 11, 2012

(54) METHOD FOR ENRICHING RARE CELL SUBPOPULATIONS FROM BLOOD

(75) Inventors: Sarah K. Olken, Belmont, MA (US); Steven A. Bogen, Sharon, MA (US); Seshi R. Sompuram, Arlington, MA (US)

(73) Assignee: Medical Discovery Partners LLC, Boston, MA (US)

( * ) Notice: Subject to any disclaimer, the term of this patent is extended or adjusted under 35 U.S.C. 154(b) by 1199 days.

(21) Appl. No.: 11/918,012

(22) PCT Filed: Apr. 4, 2006

(86) PCT No.: PCT/US2006/012595
§ 371 (c)(1),
(2), (4) Date: Mar. 31, 2008

(87) PCT Pub. No.: WO2007/092028
PCT Pub. Date: Aug. 16, 2007

(65) Prior Publication Data
US 2009/0081632 A1    Mar. 26, 2009

Related U.S. Application Data

(60) Provisional application No. 60/669,388, filed on Apr. 8, 2005.

(51) Int. Cl.
*C12N 5/00* (2006.01)
*C12N 5/02* (2006.01)

(52) U.S. Cl. .................................. 435/378; 435/325

(58) Field of Classification Search .................. 435/378
See application file for complete search history.

(56) References Cited

U.S. PATENT DOCUMENTS

| | | |
|---|---|---|
| 3,902,964 A | 9/1975 | Greenspan |
| 4,097,237 A | 6/1978 | Oberhardt et al. |
| 4,181,609 A | 1/1980 | Wardlaw et al. |
| 4,675,286 A | 6/1987 | Calenoff |
| 4,752,563 A | 6/1988 | Kortright et al. |
| 4,752,582 A | 6/1988 | Vanderlaan et al. |
| 4,927,756 A | 5/1990 | Schwengers |
| 4,933,092 A | 6/1990 | Aunet et al. |
| 4,940,668 A | 7/1990 | Wardlaw et al. |
| 4,994,192 A | 2/1991 | Corin et al. |
| 5,118,428 A | 6/1992 | Sand et al. |
| 5,437,987 A | 8/1995 | Tens et al. |
| 5,482,829 A | 1/1996 | Kass et al. |
| 5,725,774 A | 3/1998 | Neyer |
| 5,766,552 A | 6/1998 | Doshi et al. |
| 5,840,502 A * | 11/1998 | Van Vlasselaer ............ 435/7.21 |
| 5,877,299 A | 3/1999 | Thomas et al. |
| 5,962,237 A | 10/1999 | Ts'o et al. |
| 6,069,014 A | 5/2000 | Schrier et al. |
| 6,187,583 B1 | 2/2001 | Milchanoski et al. |
| 6,280,622 B1 | 8/2001 | Goodrich et al. |
| 6,365,362 B1 | 4/2002 | Terstappen et al. |
| 6,448,075 B1 | 9/2002 | Thomas et al. |
| 6,491,917 B1 | 12/2002 | Thomas et al. |
| 6,750,326 B2 | 6/2004 | Thomas et al. |
| 6,872,567 B2 | 3/2005 | Thomas et al. |
| 6,933,148 B2 | 8/2005 | Collins et al. |
| 6,949,355 B2 | 9/2005 | Yamanishi et al. |
| 2002/0009440 A1 | 1/2002 | Thomas et al. |
| 2004/0062766 A1 * | 4/2004 | Collins et al. .............. 424/144.1 |

OTHER PUBLICATIONS

Allard et al., *Clinical Cancer Research*, vol. 10, p. 6897-6904 (2004).
Bilkenroth et al., *Int. J. Cancer*, vol. 92, p. 577-582 (2001).
Brandt et al., *Int. J. Cancer*, vol. 76, p. 824-828 (1998).
Braun et al. *Int. J. Cancer (Pred. Oncol.)*, vol. 84, p. 1-5 (1999).
Choesmel et al., *Cancer*, vol. 101, No. 4, p. 693-703 (2004).
Cristofanilli et al., *The New England Journal of Medicine*, vol. 351, p. 781-791 (2004).
Dean et al., *The Journal of Immunology*, vol. 115, p. 1449-1455 (1975).
Despres et al., *Journal of Hematotherapy & Stem Cell Research*, vol. 9, p. 557-564 (2000).
Doyle et al., *J. Clin. Oncol.* Abstract 2004 ASCO Annual Meeting (2004).
Engel et al., *British Journal of Cancer*, vol. 81(7), p. 1165-1173 (1999).
Fehm et al., *Cytotherapy*, vol. 7, No. 2, p. 171-185 (2005).
Gala et al., *Clinical Chemistry*, vol. 44(3), p. 472-481 (1998).
Ghossein et al., *Journal of Clinical Oncology*, vol. 13, No. 5, p. 1195-1200 (1995).
Hermann et al., *Biochem. Exp. Biol.*, p. 365-368 (1977).
Hildebrandt et al., *Transfusion*, vol. 40, p. 507-512 (2000).
Klein et al., *The Lancet*, vol. 360, p. 683-689 (2002).
Kraeft et al., *Clinical Cancer Research*, vol. 6, p. 434-442 (2000).
Kruger et al., *Transfusion*, vol. 40, p. 1489-1493 (2000).
Lacroix et al., *Int. J. Cancer*, vol. 92, p. 1-8 (2001).
Laribi et al., *Eur. Urol.*, vol. 39, p. 65-71 (2001).
Martin-Henao et al., *Transfusion*, vol. 40, p. 35-43 (2000).
Martin et al., *Experimental Hematology*, vol. 26, p. 252-264 (1998).
Liberti et al., *Journal of Magnetism and Magnetic Materials*, vol. 225, p. 301-307 (2001).

(Continued)

*Primary Examiner* — Ruth Davis
(74) *Attorney, Agent, or Firm* — Steptoe & Johnson LLP

(57) ABSTRACT

An antigen-dependent negative selection blood cell separation method is described. Rare circulating epithelial cells can be separated from blood by depleting erythrocytes from a blood sample. Erythrocytes are depleted by agglutination. The new method comprises the use of an agglutinating agent, such as an anti-glycophorin A or glycophorin B antibody, as glycophorin A or B are present on erythrocytes and not on the desired epithelial cells. With regular mixing, desired rare circulating epithelial cells do not become entrapped in the red cell agglutinate.

17 Claims, 8 Drawing Sheets

OTHER PUBLICATIONS

Lewis et al., *Cytometry*, vol. 23, p. 218-227 (1996).
Mehes et al., *American Journal of Pathology*, vol. 159, p. 17-20 (2001).
Meye et al., *International Journal of Oncology*, vol. 21, p. 521-530 (2002).
Naume et al., *Cytotherapy*, vol. 6, p. 244-252 (2004).
Nicola et al., *Blood Cells*, vol. 6, p. 563-579 (1980).
Nitta et al., *Cancer Research*, vol. 47, p. 4877-4883 (1987).
Pachmann et al., *Clin. Chem. Lab. Med.*, vol. 43, p. 617-627 (2005).
Pantel et al., *Journal of the National Cancer Institute*, vol. 85, No. 17, p. 1419-1424 (1993).
Pertoft et al., *Experimental Cell Research*, vol. 50, p. 355-368 (1968).
Racila et al., *Proc. Natl. Acad. Sci.*, vol. 95, p. 4589-4594 (1998).
Rasamoelisolo et al., *Vox Sang.*, vol. 72, p. 185-191 (1997).
Reid et al., *TCB*, vol. 1, p. 57-64 (1997).
Reid et al., *Transfus Clin. Biol.*, vol. 9, p. 63-72 (2002).
Ring et al., *British Journal of Cancer*, vol. 92, p. 906-912 (2005).
Ring et al., *The Lancet*, vol. 5, p. 79-88 (2004).
Rodriguez-Salas et al., *Acta Cytologica*, vol. 44, p. 237-241 (2000).
Sabile et al., *Am. J. Clin. Pathol.*, vol. 112, p. 171-178 (1999).
Siewert et al., *Recent Results in Cancer Research*, vol. 158, p. 51-60 (2001).
Simpson et al., *Prenatal Diagnosis*, vol. 15, p. 907-912 (1995).
Skoog et al., *Blood*, p. 436-454 (1956).
Smith et al., *Developmental Biology*, vol. 27, p. 434-441 (1972).
Soeth et al., *Cancer Research*, vol. 57, p. 3106-3110 (1997).
Sompuram et al., *Clinical Chemistry*, vol. 48, p. 410-420 (2002).
Sompuram et al., *Journal of Histochemistry & Cytochemistry*, vol. 50(11), p. 1425-1433 (2002).
Sompuram et al., *Journal of Histotechnology*, vol. 26(2), p. 117-123 (2003).
Verloes et al., *Arch Int Physiol Biochim*, vol. 84(2), p. 418-420 (1976).
Wang et al., *Cancer*, vol. 88 (12), p. 2787-2795 (2000).
Werther et al., *Journal of Immunological Methods*, vol. 238, p. 133-141 (2000).
Zippelius et al., *Clinical Cancer Research*, vol. 6, p. 2741-2750 (2000).
Zigeuner et al., *Journal of Urology*, vol. 164, p. 1834-1837 (2000).

\* cited by examiner

Filter holder with stainless steel screen support

METHOD FOR ENRICHING RARE CELL SUBPOPULATIONS FROM BLOOD

CLAIM OF PRIORITY

This application claims priority under 35 U.S.C. §371 to International Application No. PCT/US2006/012595, filed on Apr. 4, 2006, which claims priority to U.S. Patent Application Ser. No. 60/669,388, filed Apr. 8, 2005, each of which is incorporated by reference in its entirety.

TECHNICAL FIELD

The present invention relates to a method of enriching rare cells from a fluid containing a mixture of rare cells and non-rare cells.

BACKGROUND

There has been growing interest in developing methods to detect and quantify circulating tumor cells from blood. Most types of cancer, such as tumors of the breast, prostate, colon, pancreas, esophagus, stomach, and liver are of epithelial origin. Blood cells, on the other hand, are of mesenchymal origin. This difference facilitates the detection of cancer cells, since epithelial-specific markers can be used to identify putative cancer cells in blood. Blood cells will not bear these epithelial-specific markers since they are not of epithelial origin. The presence of circulating tumor cells can be of clinical value in detecting cancer at an early stage, where surgical intervention can be curative. In addition, the presence and number of circulating tumor cells can be of value in cancer patient staging or prognosis, providing an indicator of which patients will likely develop metastases.

There is now considerable evidence that carcinomas shed neoplastic cells into the circulation. This evidence includes studies employing immunomagnetic separation methods to recover circulating epithelial cells from blood [Racila, E., et al. *Proc. Natl. Acad. Sci. USA*. (1998) 95:4589-4594; Engel, H., et al. *Br. J. Cancer*. (1999) 81:1165-1173; Kraeft, S.-K., et al. *Clin. Cancer Res*. (2000) 6:434-442; Wang, Z.-P., et al. *Cancer*. (2000) 88:2787-2795; Brandt, B., et al. *Int. J. Cancer*. (1998) 76:824-828; Bilkenroth, U., et al. *Intl J. Cancer*. (2001) 92:577-582.] as well as those that probe for tumor-specific mRNA in the blood cells of cancer patients. [Lacroix, J., et al. *Int. J. Cancer*. (2001) 92:1-8; Ghossein, R., et al. *J Clin Oncol*. (1995) 13:1195-1200; Soeth, E., et al. *Cancer Res*. (1997) 57:3106-3110; Laribi, A., et al. *European Urology*. (2001) 39:65-71; Kruger, W., et al. *Transfusion*. (2000) 40:1489-1493.] The number of circulating neoplastic cells increases with tumor stage. The ability of these cells to establish distant metastatic foci is unclear. Many circulating tumor cells (CTCs) are apoptotic. [Mehes, G., et al. *Amer. J. Pathol*. (2001) 159:17-20.] It is likely that the cells circulate for hours or days until they are either trapped in the pulmonary vasculature or die. It is probably the rare, exceptional circulating tumor cell that forms a distant metastatic tumor focus.

The rate of neoplastic cell shedding from a solid tumor is undoubtedly quite low, especially in the early stages of tumor growth. Detecting rare CTCs is technically challenging. The success rate depends upon the patients' clinical stage. Isolating CTCs in late-stage neoplastic disease is easier, as there are more of them. In fact, in severe cases, they can even be evident on a routine peripheral blood smear, without any enrichment whatsoever. [Rodriguez-Salas, N., et al. *Acta Cytologica*. (2000) 44:237-41.] Not all investigators have found CTCs in stage I (localized) disease. The reason for the conflicting findings can relate to the methodologies that have been employed. Subtle methodologic variables have been described that probably account for past discrepant results. [Kruger, W., et al. *Transfusion*. (2000) 40:1489-1493; Gala, J.-L., et al. *Clin Chem*. (1998) 44:472-481; Zippelius, A., et al. *Clin. Cancer Res*. (2000) 6:2741-2750.] Investigators who have employed novel methods to overcome these obstacles have reported circulating neoplastic cells in patients with localized (non-metastatic) tumors. These novel methods include unique cell separation technologies [Racila, E., et al. *Proc. NatL. Acad. Sci. USA*. (1998) 95:4589-4594.], combining immunomagnetic enrichment with RT-PCR detection [Kruger, W., et al. *Transfusion*. (2000) 40:1489-1493.], or highly selective primers for specific types of epithelial cells. [Lacroix, J., et al. *Int. J. Cancer*. (2001) 92:1-8; Laribi, A., et al. *European Urology*. (2001) 39:65-71.]

Identifying and quantifying circulating carcinoma cells (malignant cells of epithelial origin) has been a technically challenging undertaking. The number of circulating cancer cells depends upon the tumor load, but it is estimated to be approximately one in 1-10 million leukocytes. Therefore, in a 5 milliliter blood sample, there may be only a handful of tumor cells.

Immunomagnetic cell separations involve attaching antibodies directed to proteins found on epithelial cells to small paramagnetic beads. When the antibody-coated beads are mixed with blood, they will attach to and surround epithelial cells. The test tube is then placed in a strong magnetic field, causing the beads to pellet to one side. After removing the blood, captured cells are retained with the beads. The ability of the method to enrich for circulating carcinoma cells would be improved if the high relative numbers of erythrocytes were not in the way. In addition, the beads can sometimes interfere with downstream analysis of the tumor cells.

The currently available methods for recovering so few cells have insufficient cell yields (recoveries), often precluding rare cell isolation and subsequent analysis. Previous immunomagnetic selection studies for capturing small cell subsets from peripheral blood described highly variable cell recovery rates of 24% [Kruger, W., et al. *Transfusion*. (2000) 40:1489-1493.], 45% [Martin-Henao, G., et al. *Transfusion*. (2000) 40:35-43.], 47% [Siewert, C., et al. *Recent Results Cancer Res*. (2001) 158:51-60.], 51% [Hildebrandt, M., et al. *Transfusion*. (2000) 40:507-512.], 57% [Martin, V., et al. *Exp. Hematology*. (1998) 26:252-264.], 60% [Werther, K., et al. *J. Immunol. Methods*. (2000) 238:133-141.], 69.5% [Despres, D., et al. *J Hematotherapy & Stem Cell Res*. (2000) 9:557-564.] 70-80% [Zigeuner, R., et al. *J. Urology*. (2000) 164: 1834-1837.], & 84% [Bilkenroth, U., et al. *Intl J. Cancer*. (2001) 92:577-582.]. The recovery rate is important because it establishes a floor on the detection capability for rare cells. The gold standard cell enrichment technology in the field is immunomagnetic enrichment using ferrofluids. The technology is manufactured by Immunicon Corp., Huntingdon Valley, Pa., and commercialized by Veridex LLC, Warren, N.J. A recent paper (2004) correlated the presence of CTCs with prognosis in breast cancer patients. [Cristofanilli, M., et al. *New Engl. J. Med*. (2004) 351:781-791.] The Veridex/Immunicon ferrofluid technology is the only FDA-cleared technology for measuring CTCs (as a prognostic indicator in breast cancer). An important limitation of the ferrofluid technology is that it appears to not be effective as a cancer screening test.

According to the inventors of the Immunicon/Veridex technology, the limitation in sensitivity can be related to their positive selection method for CTC isolation. [Allard, W., et al. *Clin. Cancer Res*. (2004) 10:6897-6904.] CTCs are enriched from blood by virtue of their expression of an epithelial cell surface marker not expressed on red and white blood cells. Most commonly, immunomagnetic beads or ferrofluids are coated with an antibody to EpCAM (epithelial cell adhesion marker), a glycoprotein mediating homophilic attachment of epithelial cells. Positive selection methods have two drawbacks. First, disseminated cancer cells are characterized by a high degree of heterogeneity with respect to surface antigens, mutations, and gene expression. [Klein, C., et al. *Lancet*. (2002) 360:683-689; Braun, S., et al. *Int. J. Cancer*. (1999) 84:1-5; Pantel, K., et al. *J. Natl. Cancer Instit*. (1993) 85:1419-1424.] With regard to EpCAM, recent data from Immunicon/Veridex investigators show that circulating tumor cells express much lower levels of EpCAM than cancer cells in the primary tumor. [Doyle, G., et al. *J. Clin. Oncol*. (2004) 22:9541.] Since EpCAM mediates intercellular attachment, tumor cells must apparently downregulate EpCAM before detaching from the primary tumor. This limits the utility of this widely-used marker for separating tumor cells from blood. Veridex has tried to address this issue by increasing the magnetic load on low-expressing cells. [Liberti, P., et al. *J Magnetism Magnetic Materials*. (2001) 225: 301-307.] Another limiting factor is that many cells often begin to undergo apoptosis after detaching from the primary. [Mehes, G., et al. *Amer. J. Pathol*. (2001) 159:17-20.] Although they can still be identified by intracellular cytokeratin, cell surface protein expression will decrease as a result.

The overwhelming preponderance of cells in blood are erythrocytes, also known as red blood cells. The two methods of separating white and red blood cells from each other are density gradient sedimentation and chemical lysis. These methods depend upon physical differences between erythrocytes and nucleated blood cells. For isolating CTCs, some believe that density gradient centrifugation is better [Sabile, A., et al. *Amer. J. Clin. Pathol*. (1999) 112:171-178.] whereas others argue that lysis is better. [Pachmann, K., et al. *Clin. Chem. Lab. Med*. (2005) 43:617-627.] Neither method is sufficiently reproducible for a CTC clinical test. There are no FDA-cleared tests for CTCs using either method.

Cell separation by density gradient sedimentation relies on a gross physical distinction, cellular density for separating nucleated cells such as CTCs and erythrocytes. Density gradient sedimentation uses media of defined density, such as Percoll or Ficoll, to separate red blood cells from other nucleated blood cells. Lymphocytes and granulocytes are buoyant on a medium of 1.077 g/ml whereas red blood cells sediment. Cultured tumor cells generally are mostly buoyant on a 1.077 g/ml density cushion, but no one has measured the density distribution of actual CTCs isolated from blood. Many bloodborne CTCs are undergoing apoptosis [Mehes, G., et al. *Amer. J. Pathol*. (2001) 159:17-20.], a factor likely to increase their cellular density. Consequently, there are significant losses associated with density gradient sedimentation. [Choesmel, V., et al. *Cancer*. (2004) 101:693-703.]

At present an acceptable level of reproducible performance (>80% recovery) with density gradients cannot be obtained. Typically only 40-50% of the starting cells are recovered. Losses occur for a variety of reasons, including the fact that some cells stick to the side of the test tube, at the interface, with a clump of red blood cells, or that some tumor cells sediment with erythrocytes. [Pachmann, K., et al. *Clin. Chem. Lab. Med*. (2005) 43:617-627.] This can possibly correlate with cell cycle, degree of apoptosis, or other unidentified factors. Other reasons include the fact that the interface is difficult to see when there are few cells, resulting in cellular losses during collection, and/or that the interface is disturbed once someone places a pipette tip in the tube and starts collecting the cells. This agitation disrupts the interface, dispersing the cells and reducing cell recovery. Some cells are also lost in the subsequent centrifugation step (after the density gradient step). The subsequent centrifugation step is for washing out the Percoll or other density media.

Certain chemical solutions (e.g., 150 mM ammonium chloride) are capable of lysing erythrocytes without substantially affecting the viability of white blood cells. Once the red blood cells are lysed, the remaining cells are sedimented by centrifugation. This technique has not been a popular one for enriching CTCs. Exposure to the lysing agent must be carefully controlled, lest nucleated cells also lyse. There are no data on the differential susceptibility of CTCs to lysing agents. Also, the process releases a massive amount of hemoglobin and red blood cells ghosts, both of which interfere with cell separation and downstream analysis.

Another way to remove unwanted cells is by a technique called "panning". An antibody to the cell type in question is allowed to adhere to a surface, such as the surface of a plastic Petri dish. When the cell mixture is layered on top of the antibody-coated surface, the targeted cells tend to tightly adhere because of the antibody-antigen reaction. Non-adherent cells are rinsed off the surface, thereby effecting a cell separation. Cells that express a cell surface protein recognized by the antibody are retained on the plastic surface whereas other cell types are not. There are two problems with this approach. First, if the red blood cells were to be removed by panning, then a large surface would be needed. There are so many red blood cells in a 5 milliliter blood sample that the surface would have to be quite large, many square meters, to physically accommodate them. In addition, tumor cells sometimes stick non-specifically to plastic surfaces at the interface of density gradients, resulting in their loss.

SUMMARY

In general, a method for enriching a cell population in a cell suspension includes removing cells that are not members of the cell population from the cell suspension. For example, a desired cell subpopulation can be isolated from blood, for analysis and possible use in clinical diagnosis. In certain circumstances, the method can be adapted to enrich cell subsets from a cell suspension, such as, for example, bodily fluids including blood, even when the cell subsets include a small fraction of the total cells in the suspension. The cell population can include rare cells. The cell suspension can be, for example, a fluid containing a mixture of rare cells and non-rare cells. The rare cells can be blood cells or non-blood cells. The rare non-blood cells can be, for example, epithelial cancer cells or cell types other than cancer cells. The cell population that is enriched can be a desired cell subpopulation from blood, which can be enriched for analysis and possible use in clinical diagnosis. Advantageously, the method is efficient, highly sensitive and reproducible. For example, one application of this invention is to the isolation of rare circulating tumor cells from erythrocytes and leukocytes, in a blood sample. The method can include mixing the cell suspension for a sufficient period of time so as to allow the cells to agglutinate without entrapping the desired rare cells. The agglutinating agent or binding reagent can be an antibody, for example, having a binding specificity for a cell surface molecule on leukocytes, such as, CD45, or an erythrocyte cell surface molecule, such as, glycophorin A and/or B. The method can include the steps of adding and removing a physiologic buffered solution to and from the erythrocyte agglutinate so as to increase the cellular recovery of non-erythrocytes.

In one aspect, a method of separating a desired non-erythrocyte cell type from erythrocytes in a cell suspension containing both erythrocytes and the desired non-erythrocyte cell type can include adding an agglutinating reagent to the erythrocyte containing cell suspension that causes erythrocytes to agglutinate, mixing the cell suspension, and separating the erythrocyte agglutinate from the desired cell type in a cell suspension in a liquid of a single, homogenous density. The agglutinating reagent does not bind to the desired non-erythrocyte cell type. The agglutinating agent can be an antibody. The antibody can have a binding specificity for glycophorin A. The method of separating non-erythrocytes from erythrocytes in a cell suspension can include adding and removing a physiologic buffered solution from the erythrocyte agglutinate so as to increase the cellular recovery of non-erythrocytes. The method of separating non-erythrocytes from erythrocytes in a cell suspension can include capturing the non-erythrocytes on a filter membrane by gravity filtration. The method can further include mounting the filter membrane onto a microscope slide. Separating the erythrocyte agglutinate from the cell suspension can include sedimenting the erythrocyte agglutinate and collecting the supernatant. Sedimenting the erythrocyte agglutinate can be performed without centrifugation. The method can further include mixing the cell suspension continuously or intermittently.

In another aspect, a method of separating a desired non-erythrocyte cell type in a cell suspension containing both erythrocytes and other undesired non-erythrocytes can include adding a first binding reagent to the cell suspension that binds to the undesired non-erythrocyte cell type, adding an agglutinating reagent to the erythrocyte containing cell suspension that causes erythrocytes to agglutinate, mixing the cell suspension, and separating the erythrocyte and undesired non-erythrocyte combined agglutinate from the desired cells in the cell suspension in a liquid of a single homogenous density. The agglutinating agent binds to the erythrocytes and the binding agent but does not bind to the desired non-erythrocyte cell type. The first binding agent can be an antibody. The antibody can bind to a cell surface molecule on leukocytes. The antibody can be directed to CD45. The first binding agent can further include a biotin moiety.

The agglutinating agent can be an antibody to an erythrocyte cell surface molecule. The erythrocyte cell surface molecule can be glycophorin A. The agglutinating agent can further include a biotin-binding moiety. The method of separating a desired cell type in a cell suspension containing both erythrocytes and other undesired non-erythrocytes can further include capturing the non-erythrocytes on a filter membrane by gravity filtration. The method can further include mounting the filter membrane onto a microscope slide. The agglutinating agent can directly bind to the first binding agent. The first binding agent and the agglutinating agent can be bound to each other prior to adding them to the cell suspension.

The method further includes the steps of adding and removing a physiologic buffered solution to and from the combined agglutinate so as to increase the cellular recovery of desired cells. Separating the erythrocyte and undesired non-erythrocyte combined agglutinate from the desired cells in the cell suspension can include sedimenting the erythrocyte and undesired non-erythrocyte combined agglutinate. Sedimenting the erythrocyte and undesired non-erythrocyte combined agglutinate can be performed without centrifugation. The method can further include the steps of adding and removing a physiologic buffered solution to and from the combined agglutinate so as to increase the cellular recovery of desired cells. The method can further include mixing the cell suspension continuously or intermittently.

In another aspect, a cell separation kit, for measuring circulating tumor cells in blood, can include an agglutinating agent that agglutinates erythrocytes in a cell suspension and instructions for processing the cell suspension. The agglutinating agent does not bind to a desired non-erythrocyte cell type. The agglutinating agent can be an antibody. The kit can further include a binding agent. The binding agent can be an antibody.

Other features, objects and advantages will be apparent from the description and the drawings.

DETAILED DESCRIPTION

Figure 1:
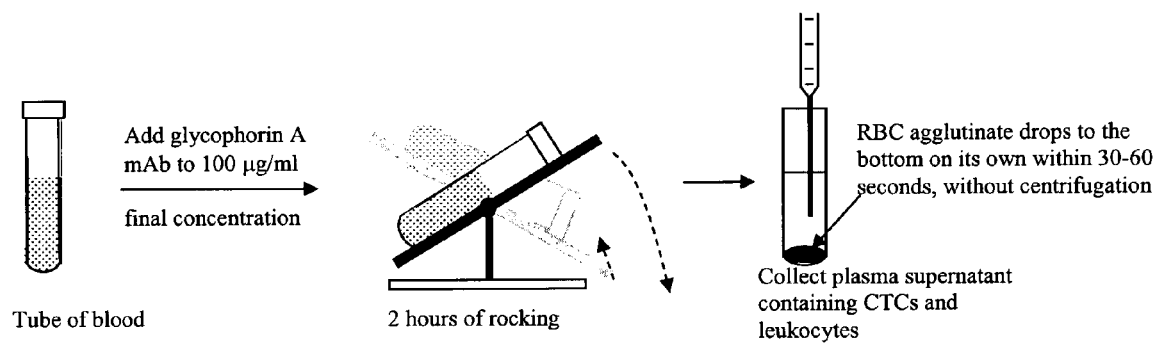
FIG. 1 is a schematic representation of the method for agglutinating red blood cells and collecting the non-depleted cells.

A method to negatively deplete blood of undesired cell types using antibodies or other crosslinking agents, without removing other nucleated cell types unless specifically desired includes one or more of the following steps. For convenience, this method of cell separation will be referred to as "cell separation by agglutination", or "CSA".

Unlike other previously described methods of separating nucleated cells from erythrocytes, such as density gradient centrifugation or chemical lysis, this method is based on the interaction of an antibody with a protein on the erythrocyte membrane. Thus, unlike the methods relying on gross physical distinctions between rare nucleated cells and erythrocytes such as density or sensitivity to chemical lysis, this method is based on an antibody's affinity for an antigen (e.g., glycophorin A). As a result, it is much more specific and has improved sensitivity in recovering rare cells. The advantages of CSA include:

Affinity-based separation. CSA removes erythrocytes with a glycophorin A-specific mAb. This is a more specific cell separation agent than a density gradient or chemical lysis agent.

Uses an intrinsic solid phase. Rather than adhering cells to beads or a plastic culture support surface, there is no new solid phase for cells to attach to. This avoids problems of non-specific adherence, as tumor cells can non-specifically attach to plastic surfaces. Introducing a new solid phase would also be impractical, as an enormous surface area of many square meters would be required to capture the ~$10^{10}$ erythrocytes in a typical blood tube. In this technique, the erythrocytes agglutinate and form such a large clump that they settle out spontaneously. There is no centrifugation.

Virtually no operator intervention. This method minimizes manipulations that can result in CTC losses. Moreover, this assay is easily adaptable to a clinical laboratory environment. Reproducibly high tumor cell recoveries (typically >90%), in tests where the blood sample is spiked with cultured breast carcinoma cells.

CSA is unique. CSA is the only antigen (e.g., glycophorin A)-dependent separation technology for isolating CTCs from both erythrocytes and leukocytes in a negative selection mode. Other antigen-dependent negative selection methods are for leukocytes only, based on depleting CD45-expressing cells. However, those methods use density gradient sedimentation or chemical lysis for removing erythrocytes, leading to excessive CTC losses.

The ability of red blood cell agglutination to separate red cells from other cell types was a surprising finding. Agglutination was previously described as separating all cell types from plasma (U.S. Pat. No. 3,902,964, which is incorporated by reference in its entirety). During agglutination, newly formed red blood cell lattices entrap other cell types, such as leukocytes that are randomly dispersed in the blood cell suspension. We confirmed that extensive non-erythrocyte cell entrapment does, in fact, occur. We also discovered that the problem can be overcome by promptly and continuously mixing the blood after adding glycophorin A mAb. If the test tube containing the blood sample is mixed immediately after adding the anti-red blood cell antibody, and kept mixing, then non-erythrocyte cell types do not become entrapped by the red blood cell lattices.

In a first embodiment, illustrated in FIG. 1, red blood cells are depleted from blood using an agglutinating agent such as an antibody that specifically binds to a protein on the red blood cell membrane. The antibody can be directed to any red blood cell-specific protein present on the cell membrane. Glycophorin A and/or B are examples of such proteins, as they are present on erythrocytes but not on other leukocytes or epithelial cells. In order to remove red blood cells, anti-glycophorin A or B antibody is added to the blood sample, at a final concentration of approximately 50-200 micrograms/ml. For optimal cell recoveries, the blood sample is collected with $Ca^{++}/Mg^{++}$-free physiologic buffer containing approximately 1-10 mM ethylenediaminetetraacetic acid (EDTA). The presence of EDTA helps prevent clotting. Heparin can optionally be used as an anti-clotting agent. The blood sample-containing test tube is mixed after adding the agglutinating antibody and then (preferably) placed on a rotating or rocking platform immediately after the antibody is added, for continuous mixing. It is important that the blood cell suspension is regularly mixed, i.e., mixed either continuously or at least repetitively (intermittently) during the incubation with the agglutinating antibody. For example, the blood cell suspension can be mixed approximately every few minutes if it is not continuously mixed. For repetitive mixing, exact intervals between mixes are helpful but not required. This is in contrast to either not mixing the sample after adding the agglutinating antibody, or only mixing once, momentarily. If the antibody is an agglutinating antibody, then a clump of red blood cells forms. Any type of mixer will be suitable to keep the blood mixing while the red blood cell clump forms. After agglutination of erythrocytes has occurred, the erythrocytes cluster into one or more clumps. When the test tube is taken off the mixer and left to stand on the benchtop, the clump(s) settle to the bottom (sediment) of the test tube, usually within one minute, without centrifugation, at 1×g (normal force of gravity). In this way, the separation of the erythrocytes from other cells in the blood cell suspension occurs without layering the blood over a density gradient. Density gradient centrifugation is one of the most common methods for separating erythrocytes from leukocytes. Instead, the separation occurs in a fluid (e.g., plasma) that is of a single homogeneous density, without an interface to another fluid that is of a different density. Red blood cell agglutinates can also be removed by using centrifugation, preferably for a short period of time and of a low g force. Red blood cell agglutinates (clumps) can be removed by any other appropriate methods. For example, the red blood cell agglutinates can be captured onto a coarse filter that retains large clumps but not monodispersed cells.

The supernatant contains all the other types of cells in blood, including leukocytes and any epithelial cells (such as carcinoma cells), if present. The supernatant also contains the blood plasma. With a pipette, the supernatant is withdrawn and transferred to another test tube.

In another embodiment, additional undesired cell types, such as leukocytes, can be removed along with the red cell clump. By removing additional undesired cell types from the blood, it will be easier to locate and analyze the desired rare carcinoma cells. Removing leukocytes can also have the added benefit of facilitating molecular expression analysis, by removing a potential source of illegitimate mRNA transcripts. Illegitimate transcripts are mRNA transcripts expressed at extremely low levels that are not transcribed into detectable levels of protein. Their presence can confound the detection of CTCs if expression analysis is used for detection. For example, cytokeratin is an epithelial marker that is not found in leukocytes. However, when extremely sensitive techniques are used for detecting mRNA for cytokeratin, extremely low levels of cytokeratin mRNA can be detected in leukocytes as well, even though the cytokeratin protein is not found in leukocytes. Therefore, the presence of leukocytes can complicate the detection of CTCs by expression analysis when so few epithelial cells are dispersed amongst millions of leukocytes. Removing them, such as through the methods described in this second embodiment, can help render expression analysis more specific for rare circulating tumor cells.

To remove leukocytes or other, undesired cell types, it is necessary to have an agglutinating agent such as an antibody or other binder that specifically binds to the cell type to be removed. For leukocytes, it can be an antibody directed to CD45, leukocyte common antigen. CD45 is present on leukocytes but not on epithelial cells. A suitable CD45-specific mAb is the one secreted by the 4B2 hybridoma, the cell line being available for purchase from the American Type Culture Collection (Manassas, Va.). Many others are available commercially.

Figure 8:
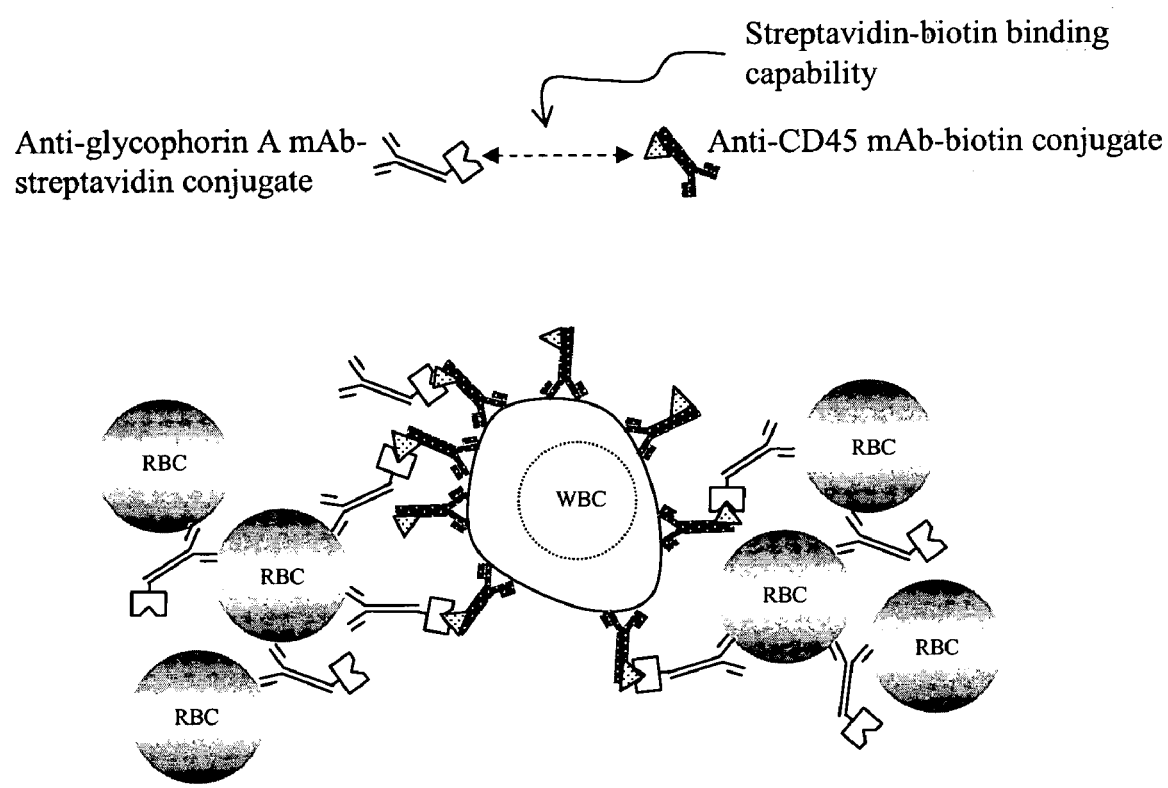
FIG. 8 is a schematic representation depicting a method to incorporate leukocytes into a red blood cell clump using a glycophorin A-streptavidin conjugate and CD45 monoclonal antibody (mAb)-biotin conjugate.

In order to remove leukocytes, a glycophorin A-specific mAb can be conjugated to streptavidin. The glycophorin A monoclonal antibody causes erythrocyte agglutination, as already described. The streptavidin moiety will bind any cell coated with biotin. Therefore, if an undesired cell type, such as a leukocyte, is coated with a binding agent such as an antibody-biotin conjugate, then it can be entrapped within the red cell aggregates and removed with the red blood cells. For example, if leukocytes are coated with an anti-CD45 antibody-biotin conjugate, then they will be caused to be bound to the streptavidin that is part of the glycophorin A antibody-streptavidin conjugate. In this way, leukocytes can be captured onto streptavidin-coated erythrocytes with biotin-conjugated leukocyte-specific mAbs (FIG. 8). In FIG. 8, "RBC" stands for red blood cell. "WBC" stands for white blood cell. The glycophorin antibody-streptavidin conjugate and leukocyte antibody-biotin conjugate are shown as illustrated at the top of the figure. The leukocyte is shown to be coated with antibodies, such as those specific for CD45. Each leukocyte antibody is conjugated to a biotin (triangles at the end of the antibody), rendering the leukocyte to be coated with biotin moieties. Any of the streptavidin proteins coating red blood cells can then bind to the biotins, tethering leukocytes to erythrocytes. As the erythrocytes agglutinate, the leukocytes become irreversibly enmeshed in the clump and are removed from the suspension.

An antibody is a type of binding agent, capable of crosslinking because of its divalent structure. Other binding agents, such as lectins, proteins, peptides, or aptamers, that can have specificity to red blood cell surface molecules can be used. It can be advantageous that whatever binding agent is used does not also bind to the cell types that are to be isolated and enriched from blood. If the binding agent is not divalent, it can be modified to be so by adding biotin. The subsequent addition of avidin, or streptavidin, then crosslinks two monovalent binding agent to form a divalent binding agent.

Although isolation from blood is shown, it is possible that this method can be used in other fluids. Rather than agglutination of erythrocytes, potentially any cell type can be caused to agglutinate in a similar way, provided that there are enough cells so as to form clusters. Therefore, this invention is not limited to the use of red blood cell-specific antibodies.

One of ordinary skill will also understand that this invention is not limited to the isolation of epithelial cells. Other cell types, or even microorganisms, can potentially be enriched from blood in this way. Although tumor cell enrichment is experimentally described, other cell types can also be enriched, whether they are rare or not.

One of ordinary skill will also understand that any erythrocyte-specific agglutinating reagent will potentially be effective in separating red blood cells from other cell types in the blood cell suspension, not just a glycophorin A-specific monoclonal antibody. For example, the antibody can be immunoreactive with glycophorin B or any other protein that will differentiate erythrocytes from other cell types in the cell suspension. Also, although an antibody is shown in the example, other types of binding agents can also be effective if they have the required red blood cell specificity and cause agglutination.

Reagent Development

The glycophorin A monoclonal antibody—streptavidin conjugate can be synthesized using conventional protein conjugation techniques. Methods of covalent conjugation are well known to those skilled in the art, and are described in textbooks such as S. S. Wong. Chemistry of Protein Conjugation and Cross-Linking. CRC Press, Boca Raton, Fla. 1993 ISBN 0-8493-5886-8, which is incorporated by reference in its entirety. In order to create the conjugate, it is first necessary to obtain the glycophorin A monoclonal antibody. Any agglutinating glycophorin A antibody should suffice. One suitable glycophorin A (and glycophorin B, as well) monoclonal antibody is the E3 glycophorin-specific monoclonal antibody, described to be immunoreactive with a peptide sequence derived from the extracellular domain of glycophorin A, close to the red cell membrane. (M J Telen, R M Scearce, B F Haynes. 1987. Human erythrocyte antigens. III. Characterization of a panel of murine monoclonal antibodies that react with human erythrocyte and erythroid precursor membranes. *Vox Sang.* 52:236-243, which is incorporated by reference in its entirety.) The antibody is commercially available from Sigma Chemical Co., St. Louis, Mo.

Many other glycophorin-specific monoclonal antibodies have been characterized and their epitopes also identified. [Reid M E. Lisowska E. Blanchard D. Section 3: Epitope determination of monoclonal antibodies to glycophorin A and glycophorin B. Coordinator's report. Antibodies to antigens located on glycophorins and band 3. [Evaluation Studies. Journal Article. Multicenter Study] *Transfusion Clinique et Biologique.* 9(1):63-72, 2002 Jan.; Rasamoelisolo M. Czerwinski M. Bruneau V. Lisowska E. Blanchard D. Fine characterization of a series of new monoclonal antibodies directed against glycophorin A. *Vox Sanguinis.* 72(3):185-91, 1997; Reid M E. Lisowska E. Blanchard D. Coordinator's report: glycophorin/band 3 and associated antigens. *Transfusion Clinique et Biologique.* 4(1):57-64, 1997, each of which is incorporated by reference in its entirety.]. Provided that the antibody causes red cell agglutination, others such as described in these journal articles can also be suitable.

Monoclonal antibodies can be grown in vitro using conventional bioreactors containing growth medium to which the hybridomas are adapted. Preferably, the hybridoma will be adapted to serum-free conditions or a low concentration of serum, such as 1% or less. Once produced, the antibodies are concentrated by ultrafiltration and purified on Protein A or Protein G.

One method for conjugating streptavidin to the glycophorin A mAb is to use a hydrazide reaction, as per published protocols, herein incorporated by reference [Hermanson, G. (1996) Academic PressSan Diego, Calif. 0-12-342336-8.] Hydrazide conjugation is particularly useful for antibody conjugations because it targets carbohydrate moieties. Carbohydrates on antibodies are found in the Fc domain. Consequently, the conjugate forms away from the antigen-binding site, maximizing antibody immunoreactivity. A potential pitfall of this approach is that not all monoclonal antibodies have carbohydrates. Some hybridomas lose their glycosyltransferases and cannot synthesize glycoproteins. Alternatively, other methods of protein conjugation, such as those that target free amines found in lysines or at the amino terminus of each protein can be used.

The conjugated protein can then be purified from unreacted precursors or undesired homoconjugates. One possible method for carrying out this purification is to use a high pressure liquid chromatography (HPLC) system with a column specially adapted for antibody purifications. One such column is the ABx BakerBond column sold by JT Baker, Phillipsburg, N.J. An alternative method is to purify the glycophorin A mAb-streptavidin conjugate through a two-step affinity chromatographic process. The conjugate can be purified on an iminobiotin column (Pierce Chemical Co., Rockford, Ill.) followed by an antigen column. Only the desired heteroconjugate will bind and elute from both columns.

Iminobiotin is a biotin derivative with a lower affinity for streptavidin, allowing elution under milder conditions. For the antigen column, the most straightforward source of antigen would be glycophorin A from Sigma Chemical Co., St. Louis, Mo. Instead of antigen (glycophorin A), an antigen affinity column comprising a peptide mimotope can be used. The peptide can be produced less expensively and to higher purities, facilitating ultimate transition to pilot production for clinical trials. The peptide for a moderate affinity, providing for mild elution conditions, can be engineered. The peptide mimotope is also less susceptible to denaturation during the conjugate elution step, since it is small and without any appreciable secondary structure. The peptide mimotope can be identified using a peptide combinatorial library screen of a phage library. Methods for screening such a library with monoclonal antibodies, in order to find peptide mimotopes, can be found in published papers and are incorporated in their entirety by reference. [Sompuram, S., et al. *Clin. Chem.* (2002) 48:410-420; Sompuram, S., et al. *J. Histochem. Cytochem.* (2002) 50:1425-34.]

A peptide mimotope column can also be useful not just for purification but also for manufacturing the glycophorin A mAb—streptavidin conjugate. A solid phase conjugation format can yield more reproducible heteroconjugates, favoring small heteroconjugates (1:1 ratio of mAb to streptavidin). A solid phase format can also be more amenable to scale-up, for clinical trials. The solid phase format can also better protect the antigen-binding site from cross-linking, better preserving antibody immunoreactivity. To prevent the antibody from covalently cross-linking to the antigen on an antigen column, the peptide can be designed with protecting groups to block reactive moieties. An alternative to an antigen or peptide mimotope column is to separate the glycophorin A antibody-streptavidin conjugate (m.w. ~200 kDa) from free (unconjugated) streptavidin (m.w. 53 kDa) by dialysis, using a dialysis membrane with a cutoff of approximately 100 kDa. Free streptavidin will diffuse out of the dialysis membrane whereas the conjugate will stay in. Other techniques for effecting the separation include a protein A or protein G column, HPLC, as previously described, or size exclusion chromatography such as using a Sephadex column.

Alternatively, to remove leukocytes as well as erythrocytes, an agglutinating reagent can include a leukocyte-specific antibody conjugated to biotin. A monoclonal antibody to CD45 can be a suitable depleting antibody for leukocytes, since epithelial cells do not express it. Other antibodies can be added or used instead of the CD45 antibody, depending upon which cell type needs to be depleted as CD45 expression level on leukocytes varies, with lymphocytes expressing more than monocytes, which in turn express more than neutrophils. Other exemplary protein antigens that can be targeted for cell depletion are CD3 and CD19 (T and B lymphocytes, respectively), CD11b (monocytes), CD 15 (myeloid cells), and CD 16 (NK/LGL cells). There are several protocols for conjugating biotin to antibodies (S. S. Wong. Chemistry of Protein Conjugation and Cross-Linking. CRC Press, Boca Raton, Fla. 1993 ISBN 0-8493-5886-8). For example, a suitable method is to add a pre-activated biotin derivative, such as biotin-hydrazide, sulfo-N-hydroxysuccinimide-biotin, both of which are available from Pierce Chemical Co., Rockford, Ill. These pre-activated biotin derivatives will bind to carbohydrates (biotin-hydrazide) or amines (sulfo-NHS-biotin) on antibodies. Briefly, the biotin derivative is reacted with the antibody at pH 7.2 for 1-4 hours, as per the manufacturer's instructions. The mixture is then placed in dialysis tubing of a 10,000 m.w. cutoff, and dialyzed against phosphate buffered saline. In this way, unreacted biotin is removed by dialysis, leaving the antibody-biotin conjugate. If a sufficient amount of biotin is added, nearly every antibody will have at least one biotin, covalently conjugated. Methods of biotin conjugation to proteins are well known to those skilled in the art.

In order to remove leukocytes along with erythrocytes, the CD45-biotin conjugate is added to the blood sample before adding the glycophorin A mAb-streptavidin conjugate. The optimal concentration of the CD45-biotin conjugate can be empirically determined, but typical working concentrations will be approximately 5-30 micrograms per ml of blood. After approximately 30-60 minutes with occasional mixing, the glycophorin A mAb-streptavidin conjugate is added at approximately 100-150 micrograms per milliliter of blood. There is no centrifugation wash step. Apart from adding the leukocyte-specific antibody(ies), the procedure is similar to that already described in the first embodiment and illustrated in FIG. 1.

In this second embodiment, there are alternative methods for removing leukocytes in addition to erythrocytes. The aforementioned description using a streptavidin and biotin linkage can be considered an indirect method of connecting leukocytes to erythrocytes. It is also possible to directly connect the glycophorin A and CD45 antibodies to each other prior to adding them to the cell suspension. Such a conjugation can be accomplished using protein conjugation methods such as homo- or heterobifunctional linkers, such as described in S. S. Wong. Chemistry of Protein Conjugation and Cross-Linking. CRC Press, Boca Raton, Fla. 1993 ISBN 0-8493-5886-8. This exemplifies the concept of directly coupling an agglutinating agent, such as a glycophorin A-specific antibody, to a binding agent specific for other undesired cells in the cell suspension, such as a CD45 antibody, in advance and then adding the two to the cell suspension together, as a conjugate. An example of this is included in the "RosetteSep" technology by StemCell Technologies (U.S. Pat. Nos. 6,872, 567, 6,750,326, 6,448,075, and 6,117,985.) The RosetteSep technology also uses an anti-glycophorin A antibody covalently bound to leukocyte-specific antibodies, such as CD45. However, that is where the resemblance ends. Other aspects of the RosetteSep technology cannot be incorporated into the present invention, as they lead to unacceptable losses of desired cells (such as circulating tumor cells). An important difference is that the RosetteSep technology does not use red blood cell-specific agglutinating antibodies. The preferred method of the RosetteSep technology, commercialized by StemCell Technologies, Vancouver, Calif., uses density gradient sedimentation for removing erythrocytes and attached leukocytes. It is therefore fraught with the same pitfalls as other antigen-independent methods of removing erythrocytes. The one clinical study that examined Rosette-Sep found a low tumor cell recovery rate, averaging 43%. [Naume, B., et al. *Cytotherapy*. (2004) 6:244-252.] There was also substantial inconsistency in the data, with some recovery rates as low as approximately 20-25%.

The indirect method of causing leukocytes to become attached to erythrocytes has the advantage of requiring only one type of glycophorin A antibody conjugate (to streptavidin). The glycophorin A antibody-streptavidin conjugate can be used with any biotin-conjugated antibody. In fact, this method is easily adaptable to depleting leukocytes (or other cell types) with a cocktail of antibodies. It only requires that the depleting leukocyte-specific antibody be biotin-conjugated, a relatively easy procedure to perform. By contrast, the direct method requires that each leukocyte-specific antibody must be covalently conjugated to the glycophorin A antibody.

Apart from the streptavidin-biotin linker system, any other set of interacting partners can be used for entrapping an undesired cell type within a red blood cell agglutinate. Thus, the linkage between the glycophorin A and CD45 antibodies (or other antibody to an undesired cell type) can be accomplished with: an anti-immunoglobulin antibody that binds to both the red and white cell-specific antibodies, or a bivalent antibody with two distinct antibody specificities, wherein one specificity is to the glycophorin A antibody (or an attached ligand) and the other specificity is to the CD45 antibody (or attached ligand), or a polyhistidine tail (at least six histidines) on one antibody and a nickel compound on the other, or a peptide attached to the CD45-specific antibody (or other antibody to an undesired cell type) that mimics the binding epitope of the glycophorin A antibody. Such a peptide can be derived from the primary sequence of glycophorin A, or it can be identified from a combinatorial peptide library using phage display, by techniques previously published [Sompuram, S., et al. *Clin. Chem.* (2002) 48:410-420.] With this arrangement, the anti-glycophorin A antibody can bind to glycophorin A on red blood cells and, at the same time, to the glycophorin A peptide mimic on the CD45 antibody, since IgG is bivalent. In this way, the glycophorin A antibody itself will also bind to leukocytes or other undesired cell types that are destined to be removed with the red blood cell clumps. The linkage between the glycophorin A and CD45 antibodies (or other antibody to an undesired cell type) can also be accomplished with other biotin-binding peptides or proteins apart than streptavidin, such as avidin and neutravidin or other streptavidin binding compounds, such as peptides that mimic the action of biotin in binding to streptavidin.

The streptavidin-biotin indirect system is preferred for reasons of simplicity and the absence of potentially competing side reactions that can decrease the effectiveness of cellular depletion.

As yet another variation on the indirect system is to use two antibodies, both of which are biotin-conjugated. As before, one antibody binds to red blood cells while the other binds to leukocytes or any other undesired non-erythrocyte. The antibodies can bind to similar types of erythrocyte or leukocyte cell surface molecules as already described, such as glycophorin A (on erythrocytes) and CD45 (on leukocytes). Without an additional reagent, the two biotin-conjugated antibodies will not have an affinity for each other. However, if streptavidin is also added to the solution, then it can act as a molecular bridge, causing the erythrocytes and leukocytes to adhere to each other. In this way, leukocytes become entrapped in erythrocyte agglutinates, forming a combined agglutinate. In practice, it would be preferable to add the biotin-conjugated leukocyte-specific antibody to the cell suspension first, giving it ample time to bind to leukocytes. Streptavidin is then added. The amount of streptavidin should be 1-5 times the molar amount of biotin-conjugated leukocyte-specific antibody. The streptavidin binds to the biotin moieties, many of which are by now attached to the leukocyte (or other undesired cell type) cell surface. After an incubation time that allows the newly-added streptavidin to bind to the biotins on leukocytes, a biotin-conjugated red blood cell agglutinating antibody is added. As the red blood cells agglutinate, they will also bind to nearby leukocytes, thereby entrapping them into the red blood cell clumps.

These reagents and associated containers or other appropriate accessories can be formulated into a kit, for cell separation and/or further analysis. Such a kit can include an agglutinating agent for performing the cell separation and instructions for the procedure. The kit can further include a binding agent. The kit can optionally also include further reagents and instructions for performing the detection, or analysis, of CTCs. Such an analysis can be either morphologic, such as after a staining procedure, or by molecular methods after examining mRNA expression.

Measuring the number and type of CTCs can be useful in detection of otherwise occult solid tumors, such as carcinomas of breast, prostate, lung, colon, esophagus, stomach, pancreas, etc. In addition, CTC quantification can be useful in staging previously-diagnosed cancer patients, predicting the aggressiveness of a tumor, or predicting the likelihood of recurrence after surgical resection. CTC detection can also be useful in detecting recurrence long after a tumor was surgically removed.

Cellular Evaluation and Identification

The resulting recovered cells can then be examined microscopically and/or through molecular genetic methods. Suitable blood stains include the Wright-Giemsa or Hematoxylin/Eosin stains. Alternatively, the cells can be stained using an antibody, such as for epithelium-specific proteins. For example, cytokeratin is an intracellular protein found in epithelial cells and not in leukocytes. Immunofluorescent or immunohistochemical stains for cytokeratin can distinguish leukocytes from epithelial cells. CTCs can be identified by a combination of three markers: cytokeratin (FITC), CD45 (allophycocyanin), and DAPI. If leukocytes are depleted using an anti-CD45 monoclonal antibody (mAb), then it is important to use a CD45 mAb that recognizes a non-interfering epitope relative to the CD45 mAb used for cell separation. Tumor cells will be enumerated by fluorescence microscopy. Cells that have a visible nucleus, are cytokeratin-positive and CD45-negative, are often considered CTCs, as per published standards in the field. [Cristofanilli, M., et al. *New Engl. J. Med.* (2004) 351:781-791; Allard, W., et al. *Clin. Cancer Res.* (2004) 10:6897-6904.]

Preferred features of each aspect of the invention are as for each of the other aspects *mutatis mutandis*. The prior art documents mentioned herein are incorporated to the fullest extent permitted by law.

The invention will be described further in the following, non-limiting examples.

EXAMPLES

Figure 2:
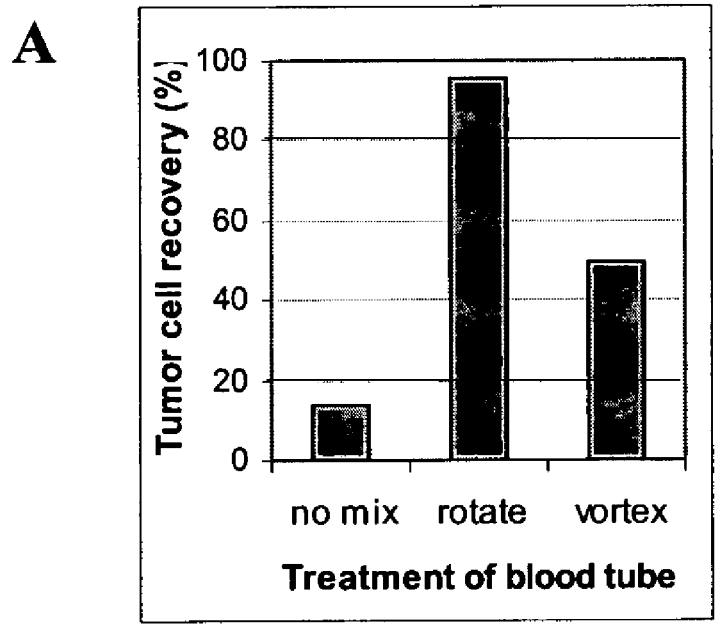
FIG. 2 shows two graphs, A and B, illustrating the relationship between tumor cell recovery from blood (spiked with cultured tumor cells) as a function of mixing the blood tube.
Figure 2:
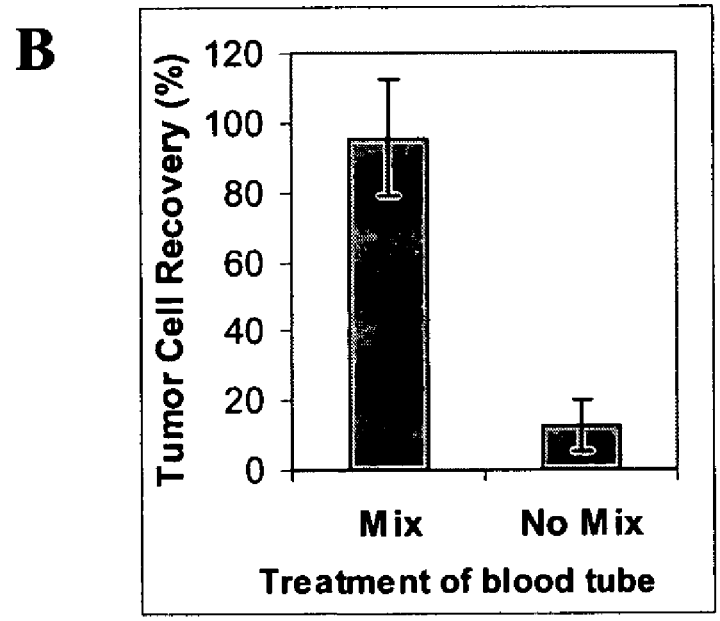

FIG. 2 illustrates the difference that mixing can make in tumor cell recoveries using blood specimens spiked with ZR-75-1 (breast carcinoma) tumor cells. Two separate experiments are shown (A and B). In the former (A), the tubes were either not mixed at all ("no mix"), mixed constantly on a rotator ("rotate"), or intermittently mixed on a vortex mixer ("vortex"). For the second experiment (B), the intermittent vortex mixing was not re-tested. The mixed group in experiment B used constant mixing on a tumbling shaker, whose motion is illustrated in the middle of FIG. 1. The vertical bar at left (experiment B) depicts tumor cell recovery with mixing (after adding the anti-glycophorin antibody). The right-hand bar demonstrates the tumor cell recovery for tubes left standing on the bench top during erythrocyte agglutination.

In these experiments, pathologic discard blood samples were procured from the Boston University Medical Center clinical laboratory, with approval and under the terms agreed upon with the Institutional Review Board for the protection of human subjects. Prior to use in experiments, a measured number of MCF-7 or ZR-75-1 cells, both breast cancer cell lines procured from the American Type Culture Collection (ATCC, Manassas, Va.) were added to the test tubes. The cells were grown in vitro as per the recommended culture conditions by the ATCC. For use in this experiment, the cells were first labeled with a fluorescent tag (CellTracker Green CMFDA, Molecular Probes, Eugene, Oreg.), as per the manufacturers instructions. To label the cells metabolically, the growth media from the flask containing the cells was removed, the flask was rinsed with incomplete media (without serum), and 10 milliliters of the metabolic labeling solution was added. The metabolic labeling solution was incubated for 30 minutes at 37° C., followed by 30 minutes at 37° C. in complete media (no label). At the end of the incubation, the tumor cells had incorporated the fluorescent tag and therefore could be easily identified by fluorescence microscopy or flow cytometry.

The tumor cells were then detached from the culture vessel by incubating in Versene (1 mM EDTA in phosphate buffered saline). After detachment, the breast cancer cells were thoroughly mixed to obtain a single cell suspension. The tumor cells were fixed by addition of 1 volume of 4% paraformaldehyde and incubation on ice for 30 minutes. The cells were then counted in a hemocytometer. The tumor cell suspension was serially diluted in media with 10% fetal bovine serum and an aliquot was added to the blood sample. The number of tumor cells added was approximately 20% of the number of leukocytes in FIG. 2A and 0.1% in FIG. 2B of the number of leukocytes in the blood.

For the data shown in FIG. 2A, the following experimental procedure was used. A blood sample was divided into three equal 0.2 milliliter aliquots in three replicate conical bottom tubes. Glycophorin A-specific antibody clone E3 (Sigma Chemical Co., St. Louis, Mo.) was added to each tube. The concentration of the anti-glycophorin antibody is not critical, provided it is sufficient to cause clumping. Red blood cell clumps form at concentrations above approximately 50 micrograms per milliliter. Higher concentrations, up to approximately 200 micrograms/ml, result in faster agglutination and clumps that are more resistant to dissolution. The tube labeled "no mix" was allowed to sit vertically on the bench at room temperature for thirty minutes. Another tube, labeled "rotate", was immediately inverted after addition of the glycophorin A-specific antibody and then placed on a rotating platform. The platform rotated at a rate of one revolution every 5-10 seconds. A third tube, labeled "vortex", was mixed using a vortex mixer after the glycophorin A-specific antibody was added. It was then placed vertically on the bench, and periodically mixed every 5 minutes using the vortex mixer.

After thirty minutes, the plasma supernatant was collected from each test tube and transferred to a separate labeled test tube. The red blood cell clumps from each group were repeatedly washed and combined with their respective supernatants. To "wash" the red blood cell clumps, a physiologic buffer, such as Hanks Balanced Salt Solution, was added to the red blood cell clumps after removal of the plasma supernatant. The clumps were again allowed to settle and the supernatant collected. The process can be repeated a desired number of times. Since the tumor cells were fluorescent, the number of breast cancer cells recovered was measured by counting an aliquot and calculating the number of fluorescent cells in each supernatant sample. Tumor cell recovery is the number of tumor cells recovered divided by the number of tumor cells that were added to the blood specimen.

FIG. 2A illustrates the tumor cell recovery in each experimental group. The data illustrates that active mixing on a rotating mixer (95% tumor cell recovery) produced a better cellular recovery than periodic mixing on a vortex mixer (50% tumor cell recovery), which is better than no mixing at all (14% tumor cell recovery). Therefore, these findings demonstrate that mixing the cell suspension is an important aspect in preventing non-specific entrapment of non-erythrocytes in the red blood cell clump. FIG. 2B shows a similar experiment, performed in triplicate as shown in FIG. 1. Both experiments produced comparable results. These data demonstrate that regular mixing, either intermittent or (preferably) constant mixing, are important for avoiding non-specific trapping of the desired cells within the forming red blood cell agglutinates.

Enrichment Factor

Table 1 shows data from a representative experiment characterizing the enrichment of tumor cells after CSA processing of blood. In this experiment, CMFDA-labeled ZR-75-1 cells were spiked into 7 ml of blood obtained from an expired blood bank red cell pack. Saline was added to the concentrated blood from the red cell pack, so as to re-establish a normal hematocrit (~45%). White blood cells were absent from the red blood cell packs; the experiment is silent on the issue of white blood cell depletion. The RBC count in the plasma supernatant is sometimes difficult to estimate because the red blood cells are clumped. The number of red blood cells in each clump can only be estimated by microscopic examination. Table 1 demonstrates that CSA creates approximately a 10.000-fold tumor cell enrichment. This figure is rounded off because of the inherent inaccuracy of the red blood cell enumeration in the plasma supernatant.

TABLE 1

| | Enrichment factor | |
|---|---|---|
| | Tumor cell count | RBC count (7 ml blood sample) |
| Whole blood, before processing | 1283 | $2.6 \times 10^{10}$ |
| Plasma supernatant, after CSA | 1148 | $\sim 2 \times 10^6$ (estimate; scattered RBC clumps) |
| Enrichment factor: | ~10,000 | 89% recovery |

Time of Mixing as a Function of Tumor Cell Recovery

Figure 3:
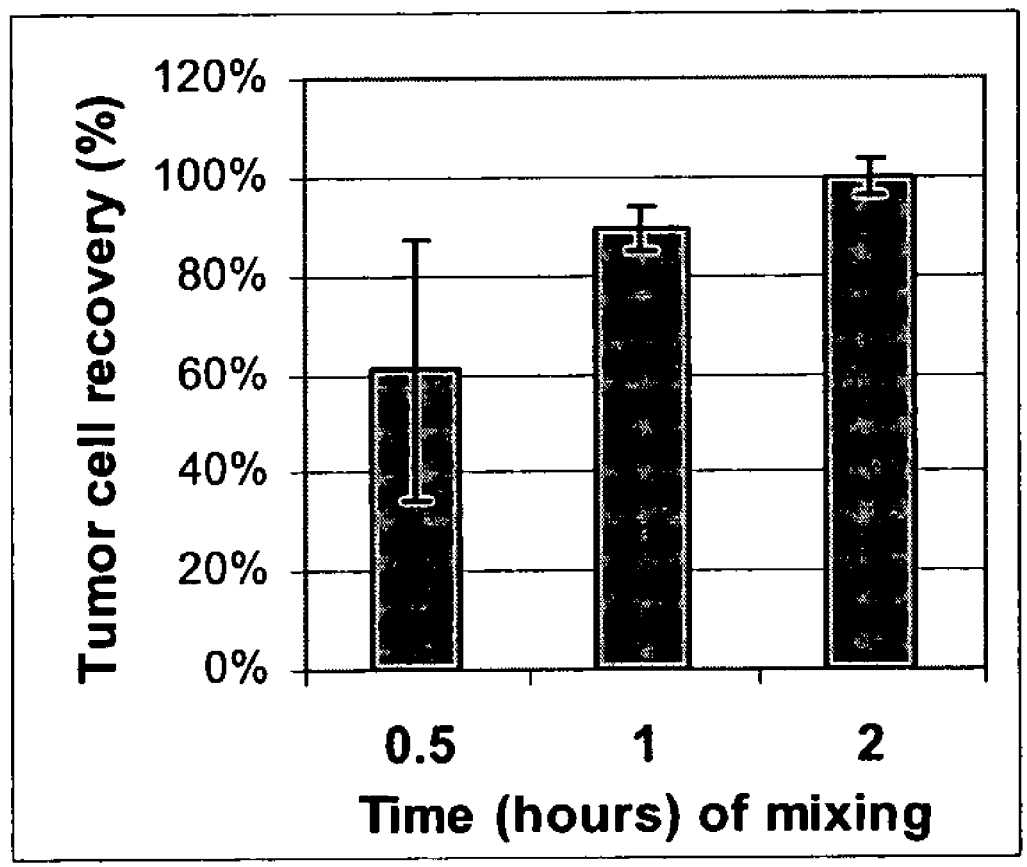
FIG. 3 is a graph illustrating the tumor cell recovery as a function of the amount of time for mixing the blood tube.

In FIG. 3, tumor cell recoveries are shown after mixing the blood with the glycophorin A mAb for variable periods of time. Fluorescently labeled ZR-75-1 (breast cancer) cells were added to blood and 7.5 ml was aliquotted into replicate tubes. As before, the blood was derived from expired and discarded blood bank red cell transfusion packs. A glycophorin A mAb was added to the blood tubes, at a final concentration of 100 micrograms per ml and mixed for 0.5, 1, or 2 hours, as shown in FIG. 3. The mean recoveries from 7.5 ml of blood are shown. ZR-75-1 tumor cells were enumerated on a fluorescent microscope. The data represent the mean±SD of duplicate samples. The data indicate that 2 hours yields the best tumor cell recovery percentage.

Increased CTC Recovery by Washing the Red Cell Clump

After collecting the supernatant, a small volume of plasma (0.2-0.3 ml) remained in and around the red blood cell pellet. It is hard to suck the pellet absolutely dry without accidentally aspirating the red blood cell clump. That small residual volume might contain some additional tumor cells. Washing the clump involves adding approximately 5 ml of physiologic buffer to the test tube containing the clump, mixing, and then removing the supernatant.

To test whether additional rinses will improve tumor cell recovery, the following experiment was conducted. Tumor cells were fluorescently labeled and added into replicate pooled pathologic discard blood samples, as previously described. The CSA protocol was then performed, as illustrated in FIG. 1. After collecting the plasma supernatant of each group, 1 volume (equivalent to the volume of blood originally) of Hanks Balanced Salt Solution (HBSS) to the red blood cell pellet was added. The tube was rocked for two minutes and then allowed the tube to stand for 30-60 seconds. The red blood cell agglutinate quickly settled to the bottom. The wash fluid (supernatant) was collected and number of tumor cells in the wash fluid was counted. The process of rinsing the red blood cell clump was repeated two more times. Tumor cells were counted in each rinse.

Figure 4:
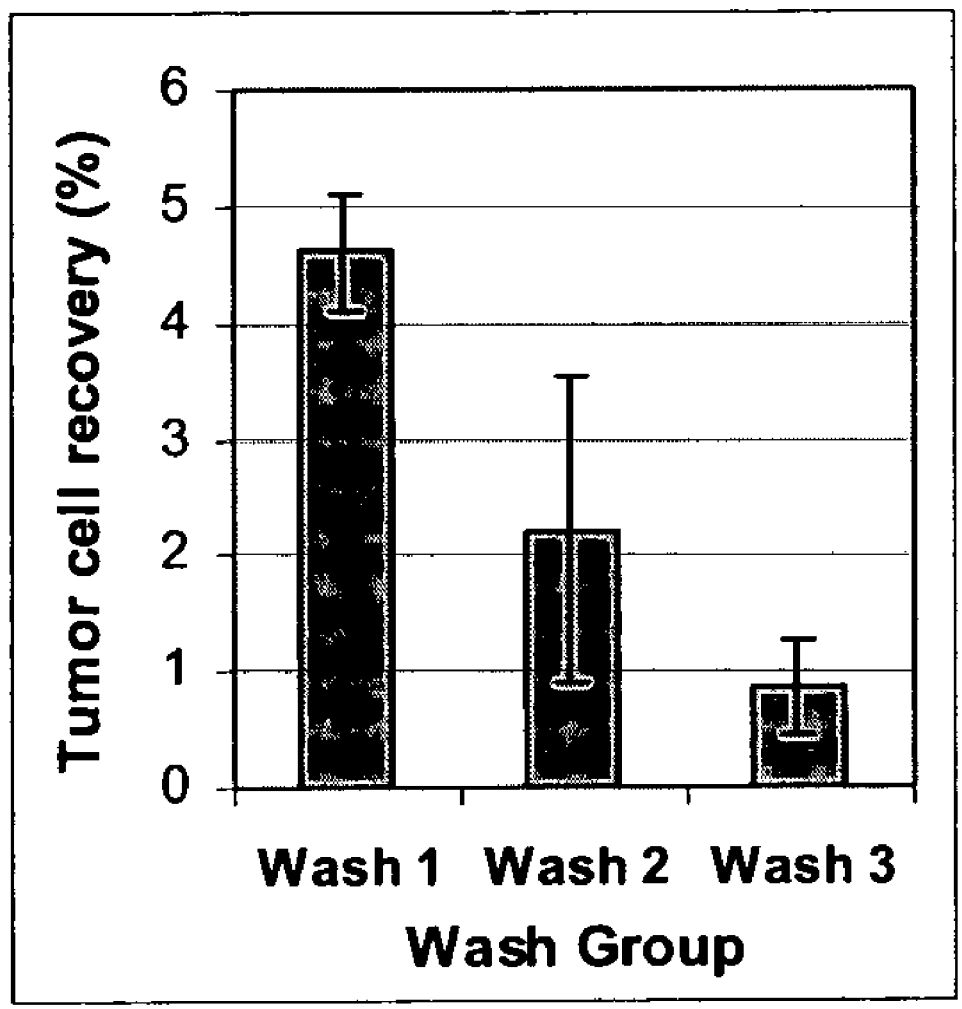
FIG. 4 is a graph illustrating the percentage of additional recovery of tumor cells by rinsing the red cell agglutinate.

FIG. 4 shows the percentage of tumor cells in each of the three serial rinses of the red blood cell agglutinate after the plasma supernatant is removed from the blood tube. Tumor cells were enumerated on a fluorescent microscope, after having been labeled prior to blood spiking experiments. The data represent the mean±standard deviation of duplicate measurements. "Wash 1" is the first rinse, after collecting the plasma supernatant containing the bulk of tumor cells. Tumor cells that remained in the residual volume of the red blood cell pellet were collected in these rinses. There are decreasing yields with each subsequent rinse. The first rinse contained the most, at approximately 4-5% of the total number of tumor cells originally added to the blood. These data lead to the conclusion that tumor cell recovery can be slightly improved, by approximately 4-5%, with a rinse of the red blood cell pellet. The rinse does not require centrifugation.

Post-CSA Tumor Cell Capture on a Solid Surface

Existing methods for mounting CTCs on microscope glass slides have been problematic, as very high cell losses can occur. Cells readily detach during the incubation steps associated with CTC identification. There is a tendency for cells coated with metal particles (immunomagnetic beads) not to stick to the slides and there are negative damaging effects of cytocentrifugation.[Kraeft, S.-K., et al. *Clin. Cancer Res.* (2000) 6:434-442; Choesmel, V., et al. *Cancer.* (2004) 101: 693-703; Meye, A., et al. *Int. J. Oncol.* (2002) 21:521-530.] Cytocentrifugation onto a glass microscope slide is reported to damage fragile CTCs.[Fehm, T., et al. *Cytotherapy.* (2005) 7:171-185.]

Centrifugation leads to loss of tumor cells. With only 10-100 tumor cells to be collected out of a tube of blood, no pellet forms, even in a conical bottom tube. When aspirating the supernatant, it is difficult to avoid aspirating the cells (and still remove all but 10-20 microliters, for subsequent application to a microscope slide). With so few cells, they do not pack into a pellet that remains at the test tube bottom. The cells are loosely suspended at the bottom of the test tube and invisible to the eye. The plasma volume (3-4 ml) is also too large for a cytocentrifuge, and centrifugation damages CTCs, as previously described.

Even if the cells could be efficiently transferred to a glass microscope slide, the cells do not firmly adhere to standard glass microscope slides, unless there is a highly adhesive slide coating. This is in contrast to a blood smear. In a blood smear, the coagulated plasma proteins entrap cells on the glass. By contrast, most blood cell enrichment protocols remove the plasma.

Figure 5:
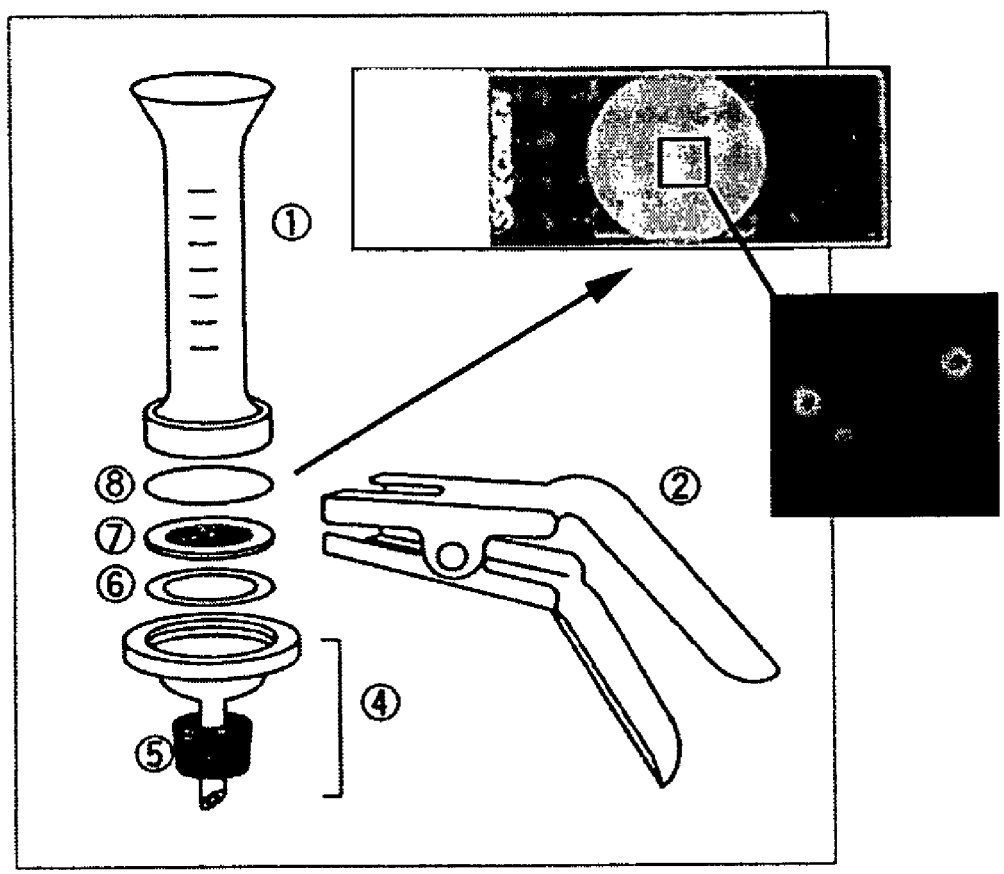
FIG. 5 is a schematic representation of the filter holder apparatus.

In order to solve this problem, a method of capturing tumor cells onto a filter membrane was developed. FIG. 5 shows how the filter is then placed on a microscope slide after it is removed from the apparatus, and how the fluorescently labeled cells appear on the filter, when viewed under a fluorescent microscope. Using a Millipore filter holder (FIG. 5), tumor cells were captured from the plasma supernatant onto a filter membrane. The supernatant was loaded into the funnel and plasma allowed to pass through by gravity filtration. Little or no suction is used. The tumor cells collected on the filter membrane as the plasma flows through. The cells were then fixed with alcohol. The membrane was then mounted on a microscope slide and coverslipped. The appearance of metabolically labeled tumor cells, captured on the filter membrane is illustrated in FIG. 5. The effect of the following variables on cell retention were tested:

1. Type of membrane. Different membrane materials, including cellulose, nylon, PVDF, and polycarbonate were tested. Polycarbonate provided minimal background fluorescence.
2. Cell adherence. Cells do not normally adhere to the membrane. However, by adding an ethanol rinse, fixing the cells in situ on the membrane, the cells remained immobilized on the filter.
3. Pore size. A pore size of 2 or 5 μm was optimal. Smaller pore sizes suffered from slower filtration rates while larger ones allowed cells to pass through.
4. Air pressure. Graded levels of suction were tested, but gravity filtration (no suction) worked best.

Figure 7:
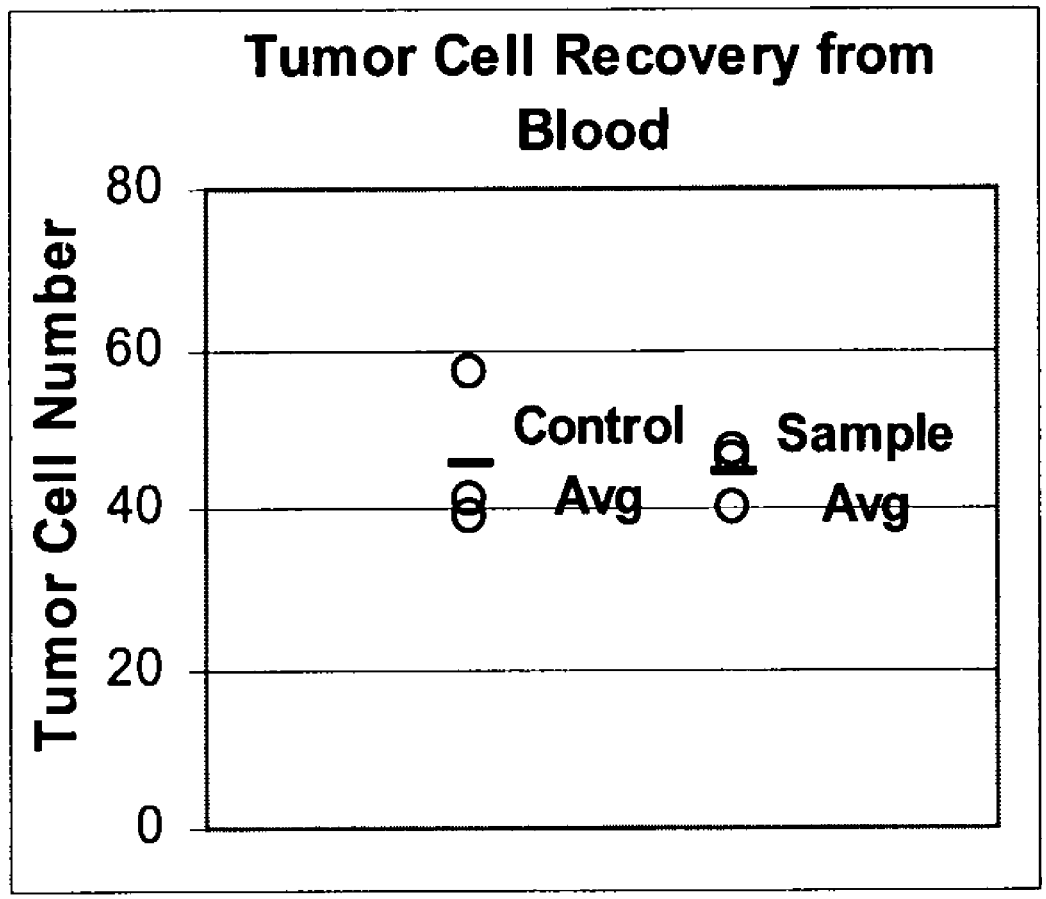
FIG. 7 is a graph showing the tumor cell recovery from blood when using membrane filtration to collect the cells.

Cell capture onto a filter membrane was first tested without the confounding variable of blood isolation. Thus, the first experiments were to test the ability of the apparatus shown in FIG. 5 to quantitatively recover tumor cells from a cell culture supernatant, regardless of any variables introduced by the presence of blood. For this first experiment, tumor cells were suspended in cell culture medium. Recovery data for tumor cells in whole blood follows next, in FIG. 7. FIG. 7 shows tumor cell recovery (from the tube of blood to which cultured tumor cells were added) onto filter membranes, comparing recovery out of blood after agglutinating and removing red blood cells (sample) with recovery out of cell culture medium (control). Varying numbers of fluorescently labeled breast cancer tumor cells (ZR-75-1 line) was added to 7.5 ml cell culture media. Table 2 shows both the expected number of cells and the actual number of recovered cells.

TABLE 2

Quantitative Recovery of Tumor Cells onto a Filter Membrane.

| No. of Tumor Cells | | | |
|---|---|---|---|
| Actual | SD (n = 3) | Expected | Recovery (%) |
| 88 | 10 | 92 | 95.7 |
| 33 | 8 | 31 | 106.5 |
| 14 | 2 | 10 | 140.0 |

Figure 6:
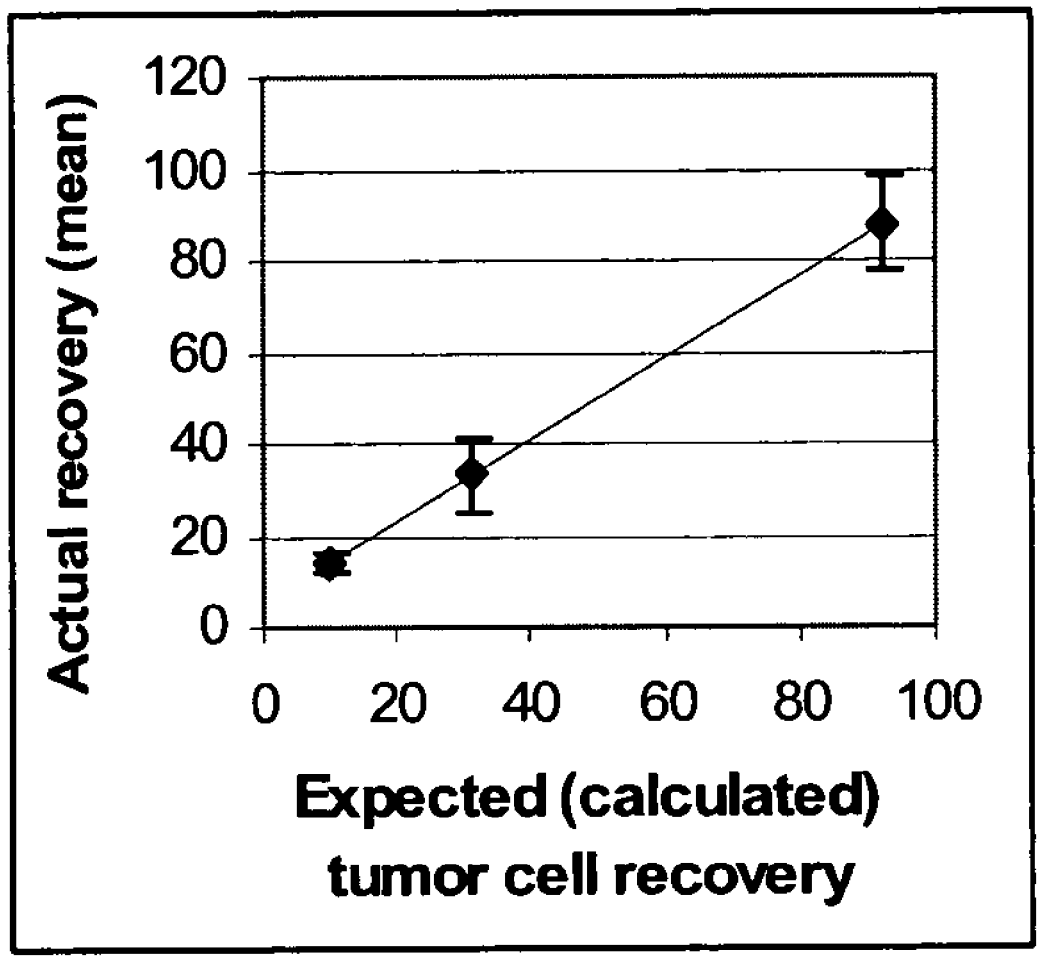
FIG. 6 is a linear regression plot showing the actual tumor cell recovery

The "Expected" cell number is calculated; the cell concentration (as determined by triplicate counts of the stock cell suspension) was multiplied by the dilution factor. The "Actual" tumor cell count is based on triplicate samples, with labeled cells being counted on the filter membranes by immunofluorescence. The 140% recovery in one group is actually a reasonable deviation when working with so few cells. The disparity between the "Actual" and "Expected" is only four (4) cells. The statistical methods change when working with so few events, as the events depart from a Gaussian distribution. FIG. 6 shows the cell recovery from tubes containing tumor cells in cell culture medium (in which the cells were grown) on filter membranes as a function of the number of tumor cells that were initially present in the tube. In FIG. 6, the slope of the regression line is 0.90 and the correlation coefficient is >0.99. These data demonstrate a nearly perfect (~100%) recovery of tumor cells onto the filter membrane from cell culture medium This filtration cell capture method was next applied to whole blood analysis. FIG. 7 shows the data for tumor cell recovery out of whole blood. This experiment is distinguished from Table 2 & FIG. 6 because it illustrates the data for tumor cell isolation from blood instead of cell culture medium. The data is from a recent experiment in which the cell recovery from samples containing approximately fifty (50) breast cancer tumor cells (ZR-75-1) added to 7.5 ml blood (from an expired and discarded red cell pack) was measured. Tumor cells were spiked into culture media ("control") or blood ("sample") at 50 cells in 7.5 ml of blood. After removing RBCs using our CSA method, tumor cells in the plasma (for the blood sample group) or tumor cells in cell culture medium (for the control group) were captured onto a filter, mounted on a slide, and counted by immunofluorescence.

The Expected cell number (not shown) is approximately fifty cells, based on the calculated number added to the media or plasma. The open circles are cell counts from individual samples and a bar shows the mean tumor cell number for each set. An average of 97% tumor cell recovery from blood was obtained, based on triplicate samples. The range is 88-103% recovery.

An alternative method for retaining cells on a microscope slide is to use a highly adhesive glass coating. Such a coating was previously described and demonstrated to have a superior ability to retain poorly adhesive tissue sections. [Sompuram, S., et al. *J. Histotechnol.* (2003) 26:1-7.] (herein incorporated by reference in its entirety). The glass slide coating technology is also described in U.S. Pat. No. 6,855,490, herein incorporated by reference in its entirety.

A number of embodiments of the invention have been described. Nevertheless, it will be understood that various modifications may be made without departing from the spirit and scope of the invention. Accordingly, other embodiments are within the scope of the following claims.

What is claimed is:

1. A method of separating a desired cell type from an erythrocyte-containing cell suspension containing both erythrocytes and the desired cell type, comprising:
   adding an agglutinating agent to the erythrocyte-containing cell suspension at a concentration that causes erythrocytes to agglutinate, wherein said agglutinating agent does not bind to the desired cell type; wherein said agglutinating agent is an antibody, wherein said antibody has the following properties: (a) the antibody binds to an erythrocyte cell surface molecule, (b) the antibody does not bind to the desired non-erythrocyte cell type and (c) said antibody causes erythrocytes to agglutinate and form erythrocyte-antibody agglutinates including said antibody;
   regularly mixing the cell suspension; and
   separating the erythrocyte-antibody agglutinates from the desired cell type in the cell suspension in a liquid of a homogeneous density.

2. The method of claim 1, wherein the erythrocyte cell surface molecule is glycophorin A or B.

3. The method of claim 1, further comprising the steps of adding and removing a physiologic buffered solution from the erythrocyte-antibody agglutinate so as to increase the cellular recovery of the desired cells.

4. The method of claim 1, further comprising the step of capturing the desired cells on a filter membrane.

5. The method of claim 4, further comprising mounting the filter membrane onto a microscope slide.

6. The method of claim 1, wherein separating the erythrocyte-antibody agglutinate from the cell suspension includes sedimenting the erythrocyte-antibody agglutinate and collecting the supernatant containing the desired non-erythrocyte cells.

7. The method of claim 6, wherein sedimenting the erythrocyte agglutinate is performed without centrifugation at 1×g.

8. The method of claim 1, wherein the cell suspension is mixed continuously after adding the agglutinating agent.

9. The method of claim 1, wherein the cell suspension is mixed intermittently after adding the agglutinating agent.

10. The method of claim 1, further comprising adding a second antibody that binds to an undesired non-erythrocyte cell type in the cell suspension, so that the undesired cell type is entrapped within the erythrocyte-antibody agglutinate.

11. The method of claim 10, wherein the second antibody binds to a leukocyte.

12. The method of claim 10, wherein the second antibody further comprises a biotin binding moiety.

13. The method of claim 10, wherein the agglutinating agent binds to the second antibody.

14. The method of claim 10, wherein the second antibody and the agglutinating agent are bound to each other prior to adding them to the cell suspension.

15. The method of claim 1 wherein the erythrocyte-containing cell suspension is a blood sample.

16. The method of claim 1 wherein the agglutinating agent further comprises a biotin binding moiety.

17. The method of claim 1 further comprising adding the agglutinating agent to the erythrocyte-containing cell suspension at a final concentration of 50-200 micrograms/ml.

* * * * *